United States Patent
Holmqvist

(10) Patent No.: US 9,095,657 B2
(45) Date of Patent: Aug. 4, 2015

(54) SELF-ADMINISTRATION MEDICAMENT DELIVERY DEVICE

(75) Inventor: Anders Holmqvist, Varmdo (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 13/641,104

(22) PCT Filed: Apr. 14, 2011

(86) PCT No.: PCT/SE2011/050456
§ 371 (c)(1),
(2), (4) Date: Nov. 1, 2012

(87) PCT Pub. No.: WO2011/133089
PCT Pub. Date: Oct. 27, 2011

(65) Prior Publication Data
US 2013/0204193 A1    Aug. 8, 2013

Related U.S. Application Data

(60) Provisional application No. 61/325,522, filed on Apr. 19, 2010.

(30) Foreign Application Priority Data

Apr. 19, 2010 (SE) ...................... 1050384

(51) Int. Cl.
*A61M 5/20* (2006.01)
*A61M 5/315* (2006.01)
(Continued)

(52) U.S. Cl.
CPC ............ *A61M 5/31528* (2013.01); *A61M 5/20* (2013.01); *A61M 5/3158* (2013.01);
(Continued)

(58) Field of Classification Search
CPC ................ A61M 5/2033; A61M 2005/206; A61M 5/3129; A61M 5/24; A61M 5/30; A61M 5/20; A61M 2005/2013; A61M 2005/202; A61M 2005/2026; A61M 2005/208; A61M 5/31533; A61M 5/31545; A61M 5/31548; A61M 5/31565; A61M 5/3158; A61M 5/31581; A61M 5/31553
USPC ......... 604/186, 294, 311, 157, 187, 192, 232, 604/146, 134–138
See application file for complete search history.

(56) References Cited

U.S. PATENT DOCUMENTS

2003/0160072 A1* 8/2003 Geiser et al. .................. 222/327
(Continued)

FOREIGN PATENT DOCUMENTS

DE      102007053742 A1    5/2009
(Continued)

OTHER PUBLICATIONS

Swedish Patent Office, Int'l Search Report in PCT/SE2011/050456, Aug. 17, 2011.
(Continued)

*Primary Examiner* — Bhisma Mehta
*Assistant Examiner* — Nilay Shah
(74) *Attorney, Agent, or Firm* — Piedmont Intellectual Property

(57) ABSTRACT

A medicament delivery device has a housing for a medicament container; a dose setting member rotatable in relation to the housing; a plunger rod acting on a stopper inside the medicament container; a driver that converts rotation of the dose setting member into translation of the plunger rod; a transversal clock spring connected to the dose setting member and to a drive member connected to the plunger rod, such that rotating the dose setting member tensions the spring; a spring hold and release member releasably connected to the drive member; and an activator having a distal end protruding through a distal passage of the dose setting member and connected to the hold and release member. Pushing the activator proximally moves the hold and release member proximally, releasing the spring from its tensioned state and forcing the drive member to rotate.

20 Claims, 8 Drawing Sheets

(51) Int. Cl.
*A61M 5/24* (2006.01)
*A61M 5/31* (2006.01)

(52) U.S. Cl.
CPC ...... *A61M 5/31553* (2013.01); *A61M 5/31583* (2013.01); *A61M 5/31535* (2013.01); *A61M 2005/202* (2013.01); *A61M 2005/2407* (2013.01); *A61M 2005/3126* (2013.01)

(56) References Cited

U.S. PATENT DOCUMENTS

2005/0137534 A1* 6/2005 Hommann .................. 604/224
2006/0276753 A1* 12/2006 Kronestedt et al. .......... 604/186
2006/0276754 A1* 12/2006 Kronestedt et al. .......... 604/186
2008/0051713 A1* 2/2008 Kohlbrenner et al. ........ 604/134
2009/0281495 A1* 11/2009 Karlsson et al. .............. 604/134
2011/0054412 A1* 3/2011 Eich et al. .................... 604/207

FOREIGN PATENT DOCUMENTS

| EP | 1728529 A1 | 12/2006 |
| WO | 2008083875 A1 | 7/2008 |
| WO | 2008098860 A1 | 8/2008 |
| WO | 2008155144 A1 | 12/2008 |
| WO | 2009092807 A1 | 7/2009 |
| WO | 2009105909 A1 | 9/2009 |

OTHER PUBLICATIONS

Swedish Patent Office, Written Opinion in PCT/SE2011/050456, Aug. 17, 2011.

* cited by examiner

SELF-ADMINISTRATION MEDICAMENT DELIVERY DEVICE

TECHNICAL AREA

The present invention relates to a medicament delivery device and in particular a device capable of delivering a pre-set dose.

BACKGROUND OF THE INVENTION

There are today numerous medicament delivery devices on the market where the main intention is to use them for self-administration of medicament. The patient or user should thus be able to use the device, whereby the device should be easy and intuitive to use for a wide range of patients from children to elderly as well as persons with reduced dexterity of the hands.

In many instances it is an advantage that different doses may be set individually by the user. This could for example be that a user should take different doses during a medication period or that the same device could be used for different persons requiring different doses, such as children and adults requiring different quantities of medicament.

It could also be an advantage that the force member, such as a spring, which is acting on a medicament container in order to expel a dose, is tensioned when a dose is set. In this way the device does not have to be stored in a highly tensioned state as often is the case with devices using spiral compression springs. Thus, the risk of damage to the devices due to creeping effects in the materials of the device is greatly reduced.

With this type of function some devices have been utilizing strip spiral springs, or clock springs, that are wound in a spiral having a central passage in which a hub is placed. Document WO 2008/155144 discloses a medicament delivery device arranged with a strip clock spring. The spring is arranged transversal in relation to the longitudinal direction of the device and is tensioned by turning a knob at the distal end of the device. When a dose of medicament is to be delivered an actuation button at the proximal end of the device is depressed whereby the clock spring is released to rotate a plunger rod, whereby the latter is moved in the proximal direction, acting on a stopper in a medicament container, such a dose of medicament is expelled.

This type of spring is particularly advantageous when the medicament has a high viscosity since such a spring usually can produce higher forces than ordinary compression springs. This type of spring is also more easily tensioned just prior to medicament dose delivery than other types of springs. However, the drawback with this type of spring is that it gives the medicament delivery device a rather large diameter at least where the spring is situated, since it is positioned transversal to the longitudinal direction and since it requires a number of windings. The thickness increases further if an activation button is to be placed in the distal end of the device. Therefore most devices with such springs have the activation button in the proximal end of the device, which sometimes is not advantageous.

BRIEF DESCRIPTION OF THE INVENTION

The aim of the present invention is to remedy the drawbacks of the state of the art medicament delivery device. This aim is obtained by the features of the patent claims.

According to a main aspect of the invention it is characterised by a medicament delivery device comprising a tubular housing arranged to accommodate a medicament container; a dose setting member being rotatable in relation to the housing for setting a dose to be expelled; a plunger rod arranged to act on a stopper inside said medicament container such that a translational movement of the plunger rod in a proximal direction causes the dose to be expelled; a drive means for converting a rotational movement of the dose setting member into translational movement of the plunger rod; a clock spring arranged transversal in relation to the longitudinal direction of the device and having a first end connected to the dose setting member and a second end connected to a drive member which is interactively connected to the plunger rod, such that the clock spring is tensioned upon rotation of the dose setting member; and a hold and release member releasably connected to the drive member for holding and—releasing the clock spring in—from a tensioned state; wherein the device further comprises activation means having a distal end protruding through a distal passage of the dose setting member, and being interactively connected to the hold and release member such that when said activation means is pushed in the proximal direction, the hold and release member is proximally moved whereby the clock spring is released from its tensioned state forcing said drive member to rotate.

According to another aspect of the invention, the activation means comprises an activation member having a distal end protruding through the distal passage of the dose setting member, and an activation sleeve coaxially arranged within the drive member, having a distal end co-acting with the activation member and a proximal end co-acting with said hold and release member.

According to yet another aspect of the invention, the tubular housing comprises a proximal and a distal housing part interactively connected to each other, and wherein the proximal housing part is arranged to accommodate the medicament container.

According to a further aspect of the invention, the drive means comprises threads as well as longitudinal grooves arranged on the outer surface of the plunger rod, radial outwardly directed protrusions on the inner surface of a central passage of the distal housing part arranged to co-act with the grooves of the plunger rod, and threads on a central passage of the drive member arranged to co-operate with the threads of the plunger rod, such that the plunger rod is locked against rotation but is movable in the longitudinal direction.

According to yet a further aspect of the invention, the inner surface of the distal housing part is arranged with first holding means interactively co-acting with corresponding first holding means of the dose setting member.

According to another aspect of the invention, the hold and release member comprises second holding means releasably connected to corresponding second holding means of the drive member such that when said dose setting member is turned to set a dose, said clock spring is tensioned and held in a tensioned state by the first and the second holding means.

According to yet another aspect of the invention, said first holding means on the inner surface of the distal housing part is a circumferentially extending ratchet and the corresponding first holding means of the dose setting member is a corresponding circumferentially extending ratchet, wherein said ratchets are formed such that said dose setting member is only rotatable in one direction and locked in a certain position when released.

According to a further aspect of the invention, the distance between two subsequent teeth of said ratchets correspond to a dose increment.

According to yet a further aspect of the invention, said dose setting member is resiliently movable in the longitudinal direction of the device by a first resilient member which is arranged between a circumferential ledge of the distal housing part and a proximal circumferential ledge of the dose setting member for forcing said ratchets in connection with each other, such that when said dose setting member is distally moved in relation to the distal housing part against the force of said second spring member, the ratchets move out of contact with each other and the dose setting member may be turned back to reset a dose.

According to another aspect of the invention, a second resilient member is arranged between an annular ledge on the inner surface of the distal housing part and a proximal annular surface of the hold and release member, and wherein the hold and release means comprises longitudinally extending grooves and ledges interactively connected to corresponding longitudinally extending grooves and ledges on the inner surface of the distal housing part, such that when said activation member is pushed in the proximal direction, the hold and release member is proximally moved but rotationally locked and when said activation member is released, said second resilient member forces the hold and release member, the activation sleeve and thereby the activation member to be distally moved.

According to yet another aspect of the invention, the second end of the clock spring is connected to the drive member through an intermediate member.

According to a further aspect of the invention, said dose setting member is arranged with an opening through which dose size indicia arranged on the drive member is visible.

There are several advantages with the present invention. Due to that the activation means is arranged through the clock spring it is possible to arrange the activation member at the distal end of the device. Further since the activation means is movable in the longitudinal direction, the hold and release member may be placed proximal to the clock spring and further the holding means are moved out of contact with each other, thereby releasing the drive member.

Preferably the drive member is arranged with indicia visible through a window such that when the dose setting member is turned in relation to the drive member, it is possible to view the set dose. Because of the use of ratchets, it is possible to turn the dose setting member in one direction and when the dose setting member is released, it is held in that position. However, the device is arranged with resetting means which is an advantage if a too large dose has been set.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
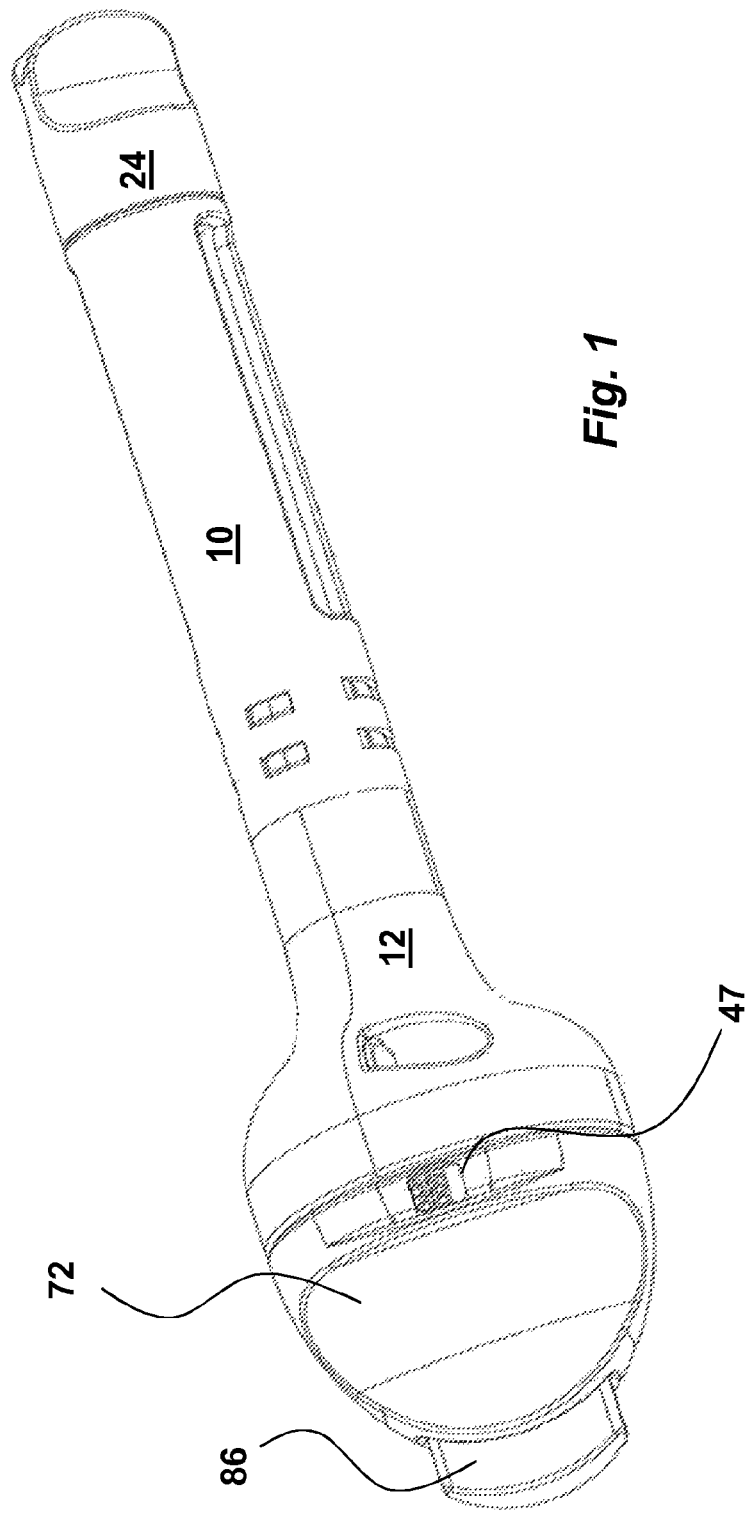
FIG. 1 is a side view of a device according to the present invention.
Figure 2:
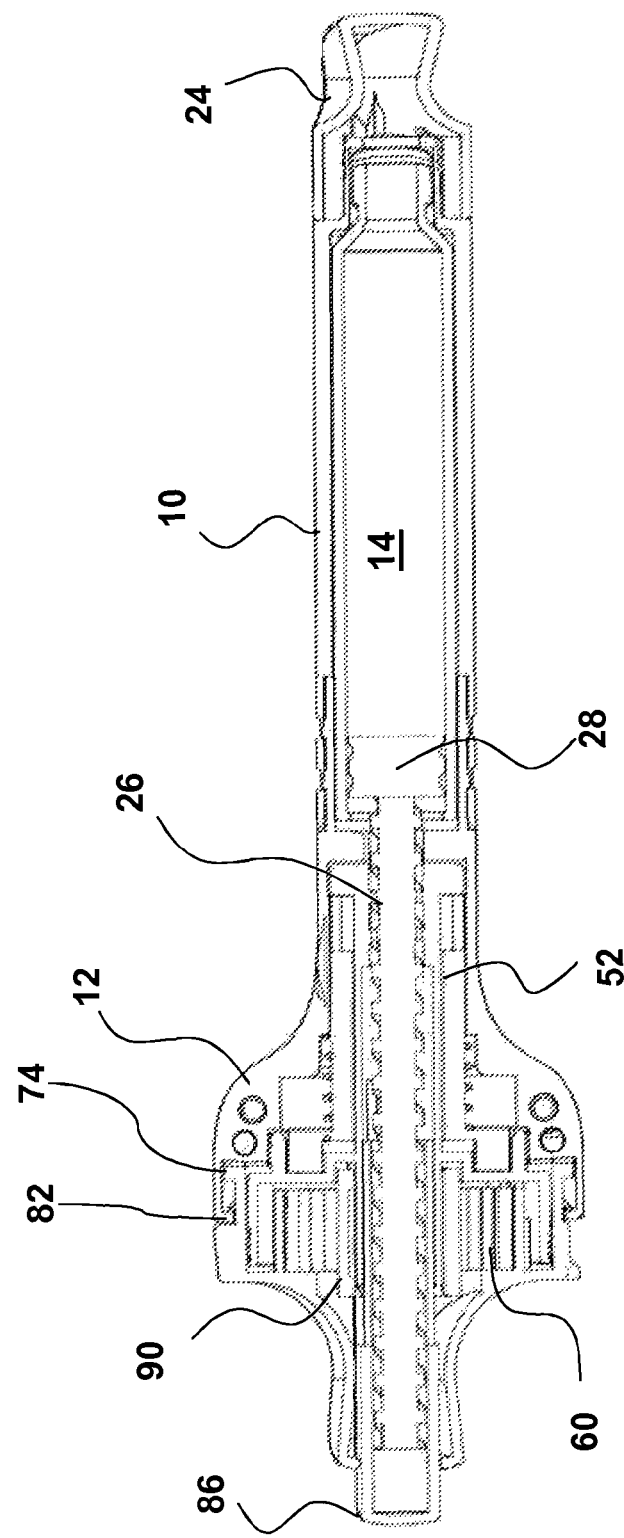
FIG. 2 is a cross-sectional view of the device of FIG. 1.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

The medicament delivery device according to the invention comprises a tubular housing arranged to accommodate a medicament container 14; a dose setting member 72 being rotatable in relation to the housing for setting a dose to be expelled; a plunger rod 26 arranged to act on a stopper 28 inside said medicament container 14 such that a translational movement of the plunger rod in a proximal direction causes the dose to be expelled; a drive means for converting a rotational movement of the dose setting member into translational movement of the plunger rod; a clock spring 60 arranged transversal in relation to the longitudinal direction of the device and having a first end connected to the dose setting member 72 and a second end connected to a drive member 38 which is interactively connected to the plunger rod, such that the clock spring is tensioned upon rotation of the dose setting member; and hold and release member 52 releasably connected to the drive member for holding and—releasing the clock spring in—from a tensioned state; wherein the device further comprises activation means having a distal end protruding through a distal passage 88 of the dose setting member 72, and being interactively connected the hold and release member such that when said activation means is pushed in the proximal direction, the hold and release member is proximally moved whereby the clock spring is released from its tensioned state forcing said drive member to rotate.

An exemplary embodiment of the present invention is shown in the FIGS. 1-8. The exemplary embodiment comprises the tubular housing comprising a proximal housing part 10 and a distal housing part 12, in the drawings shown in two halves for assembly reasons. It is however to be understood that there may be more or less housing parts depending on the actual design and manufacturing and assembly aspects.

Figure 3:
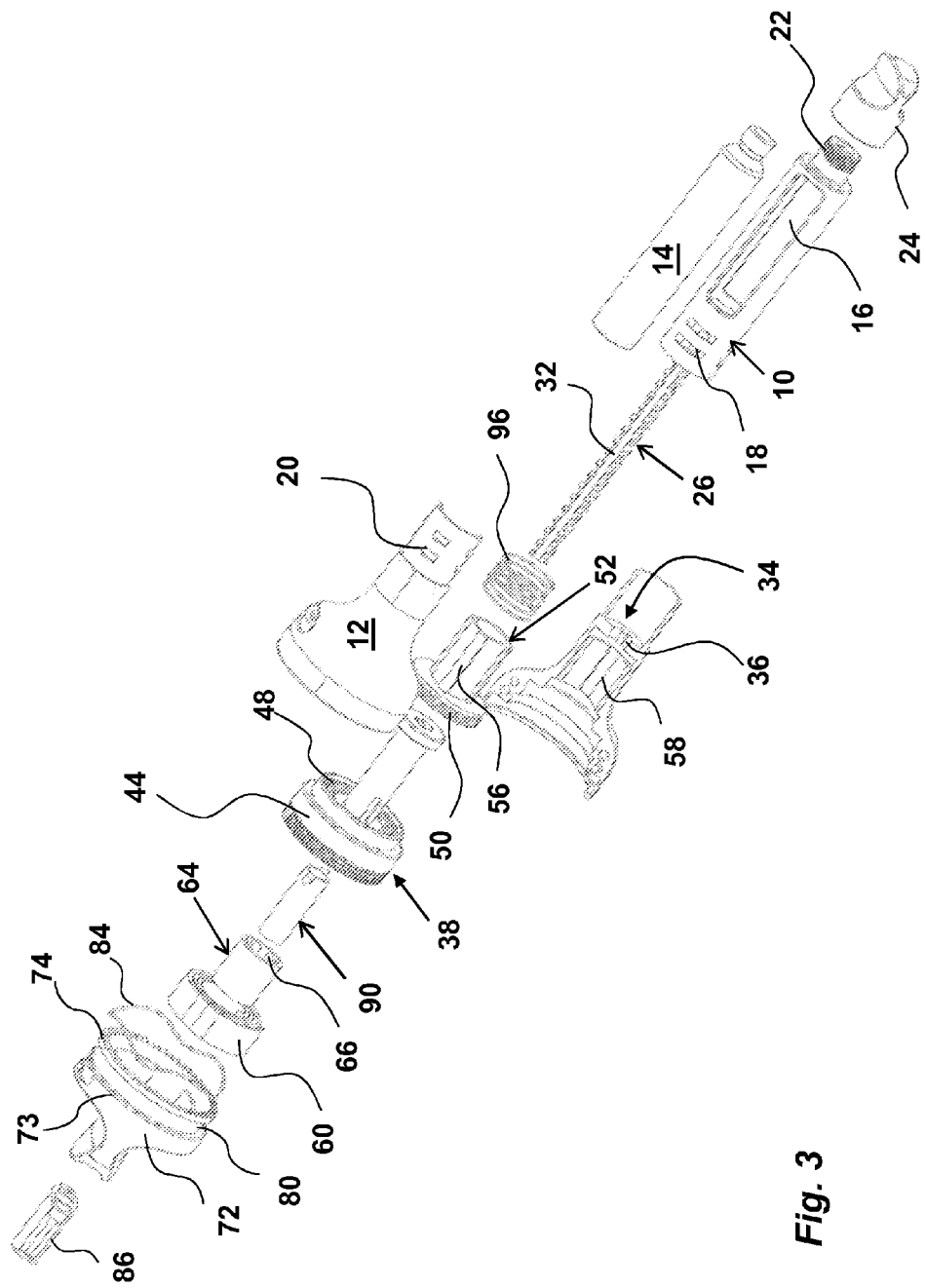
FIG. 3 is an exploded view the device of FIG. 1.

In the proximal housing part the medicament container 14 may be placed. In that aspect, the proximal housing part is arranged with longitudinal openings 16 where the medicament container may be viewed. Preferably the medicament container is transparent so that the medicament is visible through the openings 16. As seen in FIG. 3, the distal end of the proximal housing part 10 is arranged with cut-outs 18, in which protrusions 20 on the proximal end of the distal housing part fit in order to lock the proximal and distal housing parts to each other. It is however to be understood that other types of locking means may be arranged and also releasable locking means if it should be possible to e.g. change the medicament container by a user.

As seen in FIG. 3, the proximal end of the proximal housing part 10 is arranged with a threaded neck 22 onto which a medicament delivery member (not shown) may be attached, such as an injection needle, a mouth or nose piece, a nozzle and the like. It is in this context to be understood that other types of connection members may be employed for the same purpose. When the delivered to the user the proximal end of the proximal housing part is arranged with a releasibly attached protective cap 24.

Figure 5:
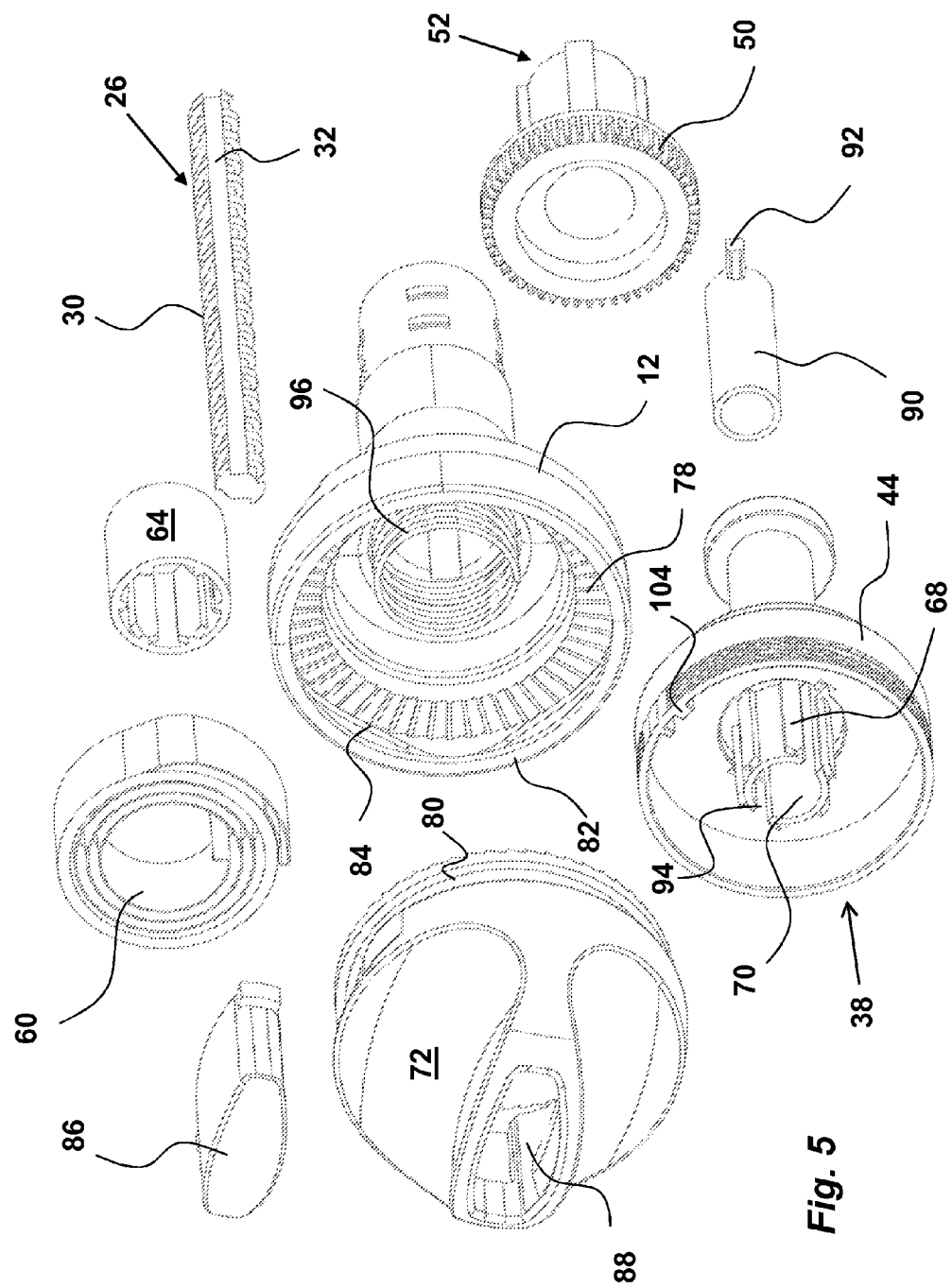
FIG. 5 is a detailed exploded view.
Figure 6:
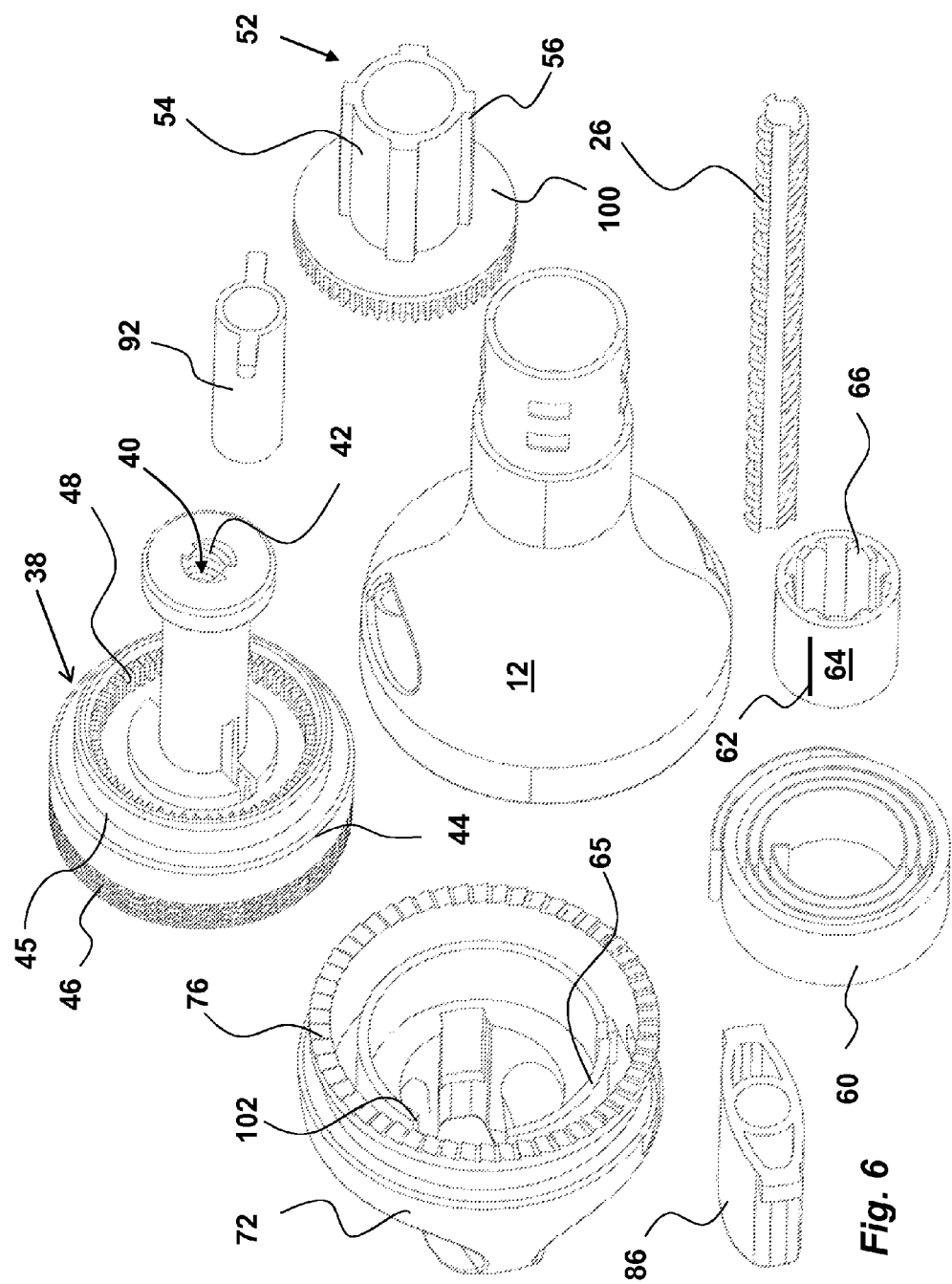
FIG. 6 is a detailed exploded view turned 180° in relation to FIG. 5.
Figure 7:
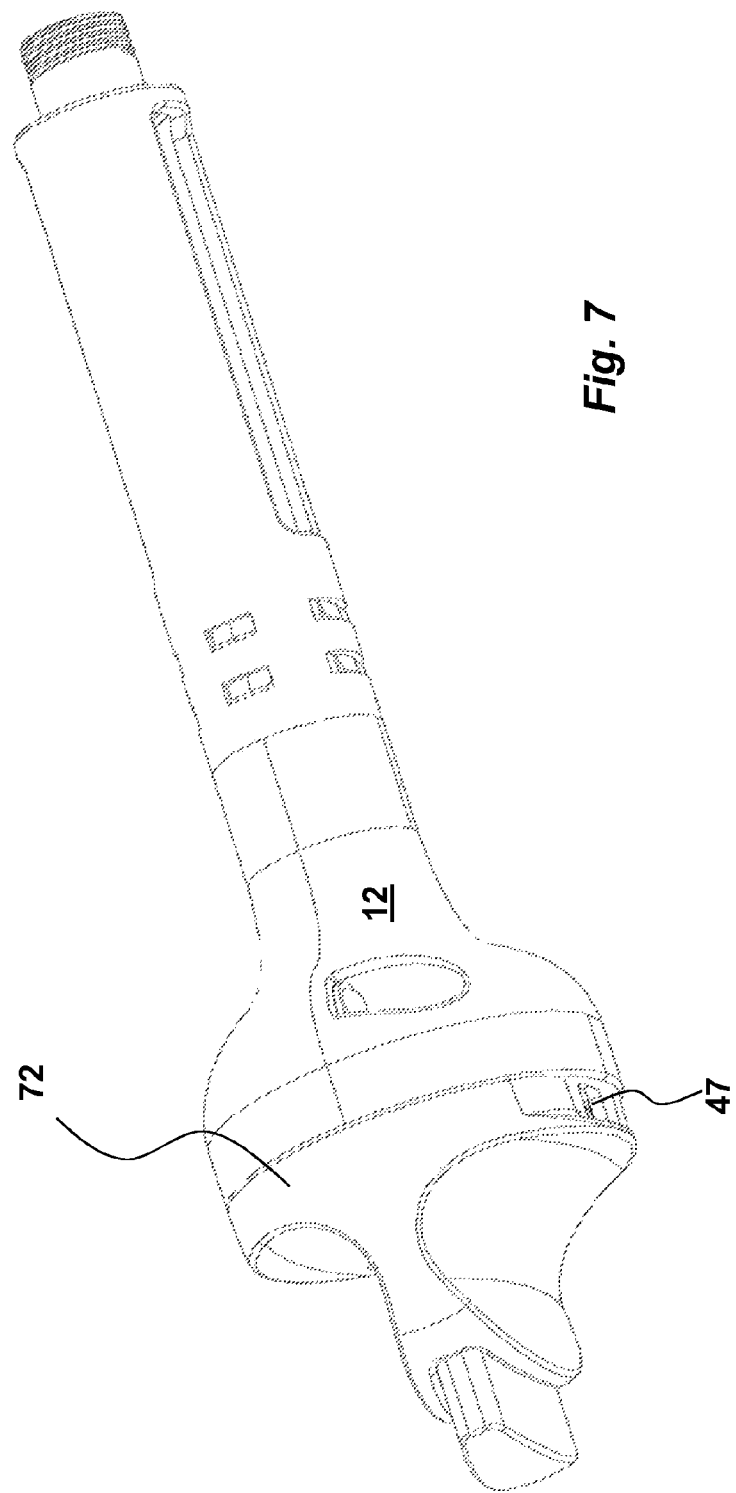
FIG. 7 is a side view of the device of FIG. 1 when an dose has been set.
Figure 8:
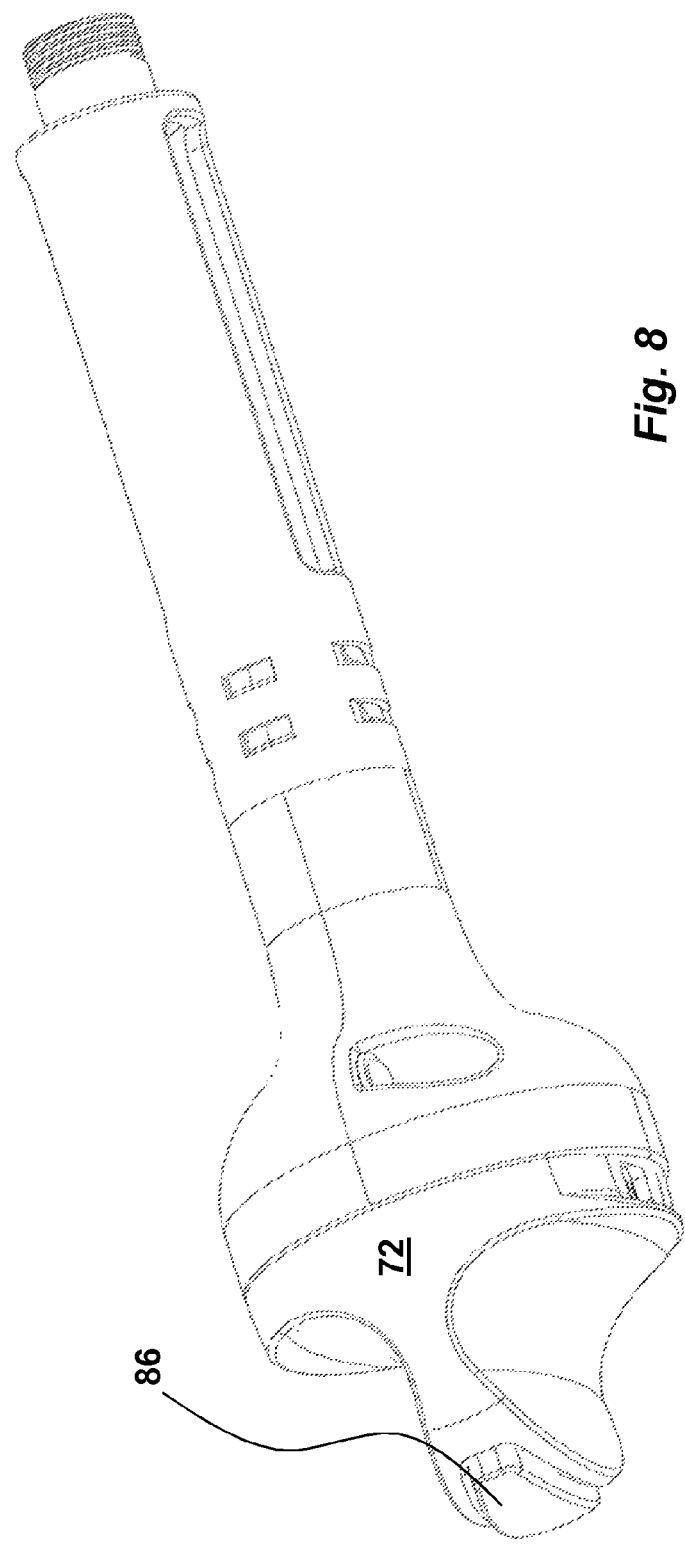
FIG. 8 is a side view of the device of FIG. 1 when an activation member has been depressed.

As seen in FIGS. 3, 5 and 6 the drive means comprises threads 30 as well as longitudinal grooves 32 arranged on the outer surface of the plunger rod 26, radial outwardly directed protrusions 36 on the inner surface of a central passage 34 of the distal housing part arranged to co-act with the grooves 32 of the plunger rod, and threads 42 on a central passage 40 of the drive member 38 arranged to co-operate with the threads 30 of the plunger rod 26, such that the plunger rod 26 is locked against rotation but is movable in the longitudinal direction.

The drive member 38 is arranged with a dose drum 44, which has indicia 46 on its outer circumferential surface. The indicia may be shown in a window 47 arranged on the dose setting member 72. As seen in FIG. 6, an annular ledge 45 extends proximally from the dose drum 44. The diameter of the annular ledge 45 being smaller than the diameter of the dose drum 44.

In the exemplary embodiment, as seen in FIG. 5, the activation means comprises an activation member 86 having a distal end protruding through the distal passage 88 of the dose setting member 72, and an activation sleeve 90 coaxially arranged within the drive member, having a distal end co-acting with the activation member and a proximal end co-acting with said hold and release member 52.

Figure 4:
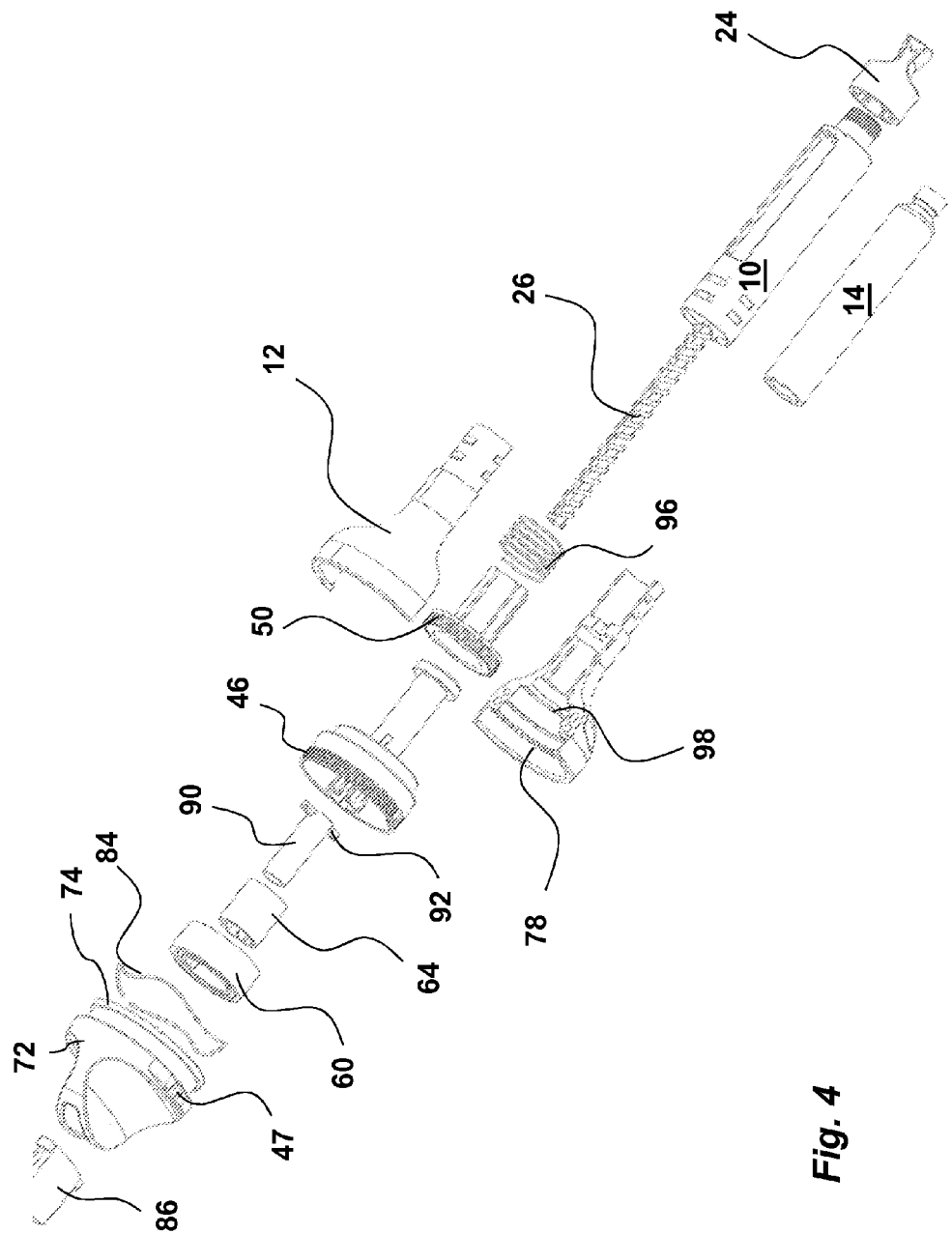
FIG. 4 is an exploded view turned 180° in relation to FIG. 3.

As seen in FIGS. 4 and 6, the inner surface of the distal housing part is arranged with first holding means 78 interactively co-acting with corresponding first holding means 76 of the dose setting member, and as seen in FIGS. 5 and 6, the hold and release member 52 comprises second holding means 50 releasably connected to corresponding second holding means 48 of the drive member 38 such that when said dose setting member is turned to set a dose, said clock spring is tensioned and held in a tensioned state by the first and the second holding means.

In the exemplary embodiment, the first holding means on the inner surface of the distal housing part is a circumferentially extending ratchet and the corresponding first holding means of the dose setting member is a corresponding circumferentially extending ratchet, wherein said ratchets are formed such that said dose setting member is only rotatable in one direction and locked in a certain position when released, and wherein the distance between two subsequent teeth of said ratchets correspond to a dose increment.

As seen in FIG. 6, the corresponding second holding means 48 are arranged to cooperate with the second holding means 50 arranged on the outer circumferential surface of the hold and release member 52, where the second holding means are longitudinal directed ledges, and where the corresponding second holding means 48 are in the form of proximally directed ledges on its inner circumferential surface of the annular ledge 45.

The clock spring 60 is of the spiral strip spring type and is arranged transversal in relation to the longitudinal direction of the device and has the first end connected to the dose setting member 72 and the second end connected to the drive member such that the spring is tensioned upon rotation of the dose setting member and whereby the hold and release member 52 is releasably connected to the drive member for holding the clock spring in a tensioned state and for releasing the clock spring from the tensioned state. However it should be understood that it is possible to have the second end of the clock spring connected to the drive member through an intermediate member 64. Also, the inner end/second end of the clock spring is fitted into, and locked, in a slit 62 of the generally tubular shaped intermediate member 64. The outer end/first end is attached to a holding member 65 arranged on the inner surface of the dose setting member. The inner surface of the intermediate member 64 is arranged with longitudinally directed grooves 66, FIG. 6, which grooves fit into protrusions 68 arranged on a distal, generally tubular shaped member 70 of the drive member 38, FIG. 5.

As seen in FIG. 3, the dose setting member 72 comprises a proximal tubular part having the corresponding first holding means 76. A circumferential groove 80 on the proximal tubular part is formed between a distal circumferential ledge 73 and a proximal circumferential ledge 74 of the dose setting member. As seen in FIG. 5, a circumferential ledge 82 is arranged on the inner surface of the distal end of the distal housing. The width of the groove 80 on the proximal tubular part is somewhat wider than the width of the circumferential ledge 82, thus locking the dose setting member to the distal housing part with a certain play in the longitudinal direction and allowing rotation of the dose setting member in relation to the distal housing part. A first resilient member 84, as e.g. a compression spring, is further arranged between the circumferential ledge 82 of the distal housing part and the proximal circumferential ledge 74 of the dose setting member such that the circumferential ratchets 76, 78 are forced in engagement with each other but may be moved out of contact with each other by pulling the dose setting member in the distal direction in relation to the distal housing part and against the force of the first resilient member, such that the ratchets move out of contact with each other and the dose setting member may be turned back to reset a dose.

In the exemplary embodiment, the proximal end surface of the activation member 86 is in contact with the distal end surface of a tubular shaped activation sleeve 90. The proximal end of the activation sleeve is arranged with transversally directed protrusions 92 that are in contact with the distal end surface of the hold and release member 52, FIG. 5. The protrusions 92 further fit into slits 94 of a distally protruding tubular member 70 of the drive member, FIG. 5. A second resilient member 96 is arranged between an annular ledge 98 on the inner surface of the distal housing part and a proximal annular surface 100 of the hold and release member 52, and the hold and release means comprises on its outer surface longitudinally extending grooves and ledges 56 interactively connected to corresponding longitudinally extending grooves and ledges 58 on the inner surface of the distal housing part, such that when said activation member 86 is pushed in the proximal direction, the hold and release member 52 is proximally moved but rotationally locked and when said activation member is released, said second resilient member forces the hold and release member 52, the activation sleeve 90 and thereby the activation member 86 to be distally moved.

The exemplary embodiment is intended to function as follows. When the device is delivered to the user, either a medicament container is already installed in the proximal housing part 10, FIG. 1, or the housing parts are separated and the user inserts a medicament container and connects the housing parts. In order to expel a dose of medicament the protective cap is removed and a medicament delivery member is exposed or attached to the neck 22. Then the dose setting member is turned 72 in relation to the distal housing part. The first quantity to be expelled may, depending on the drug, be a priming quantity in order to remove any air trapped inside the container or be a dose to be delivered to a patient.

In any event, the user is beforehand instructed how far the dose setting member 72 should be turned, which is displayed in the window 47, preferably showing indicia 48 regarding an actual dose volume. Because of the design of the first and second circumferential ratchets 76, 78, the teeth ride over each other against the force of the spring 84 in the dose setting direction. However, if the user releases the grip of the dose setting member, it is locked in that position by the design of the teeth. Should the user accidentally have turned the dose setting member 72 past a prescribed dose, it is possible to turn the dose setting member back by pulling the dose setting member in the distal direction against the force of the spring 84 whereby the teeth of the ratchets 76, 78 move out of contact with each other, enabling a turning of the dose setting member in the opposite direction.

When setting a dose, the turning of the dose setting member 72 causes the clock spring 60 to be tensioned because the outer end of the clock spring is attached to the holding member 65, and where the inner end of the clock spring 60 is attached to the intermediate member 64 with the slit 62. The intermediate member 64 is locked against rotation because its grooves 66 cooperate with the protrusions 68 on the distal member 70 of the drive member 38, which in turn is locked against rotation because the engagement between its second holding means 48 and the corresponding second holding means 50 of the tubular part, where the latter is rotationally locked by its grooves and ledges 56 fitting into the grooves and ledges 58 of the distal housing part.

When now a dose of medicament is to be expelled through the dose delivery member, the user depresses the activation member 86 in the proximal direction at the distal end of the device. The proximal movement of the activation member causes the activation sleeve 90 also to move in the proximal direction because of the contact between the two. The activation sleeve 90 moves in relation to the drive member 38, whereby the protrusions 92 move in the longitudinal slits 94 of the drive member 38. Since the protrusions 92 are in contact with the distal end surface of the hold and release member 52, the latter will move in the proximal direction, causing the second holding means 48, 50 to move out of contact with each other, against the force of the second resilient member 96. Thereby the drive member 38 is free to rotate and will do so because the clock spring 60 acting on the intermediate member 64, which is rotationally locked to the drive member 38.

Because of the threaded engagement between the drive member and the plunger rod 26, and because of the rotational lock of the plunger rod 26 by the protrusions 36 of the distal housing part 12, the rotation of the drive member 38 will cause the plunger rod 26 to move in the proximal direction, whereby the stopper 28 is also pushed in the proximal direction and a dose of medicament is delivered through the medicament delivery member until a stop ledge 102 on the inner end surface of the dose setting member 72 is moved in contact with ribs 104 on the inner annular surface of the dose drum 44. When a new dose is to be delivered the user performs the above setting and activation of the device.

It is to be understood that the embodiment described above and shown in the drawings is to be regarded only as a non-limiting example of the present invention and that it may be amended in many ways within the scope of the patent claims.

The invention claimed is:

1. A medicament delivery device, comprising:
   a tubular housing configured for accommodating a medicament container;
   a dose setting member rotatable in relation to the housing for setting a dose to be expelled;
   a plunger rod configured for acting on a stopper inside the medicament container, such that a translational movement of the plunger rod in a proximal direction causes the dose to be expelled;
   a driver that converts a rotational movement of the dose setting member into translational movement of the plunger rod;
   a spiral-strip clock spring transverse to a longitudinal direction of the device having a first end connected to the dose setting member and a second end connected to a drive member interactively connected to the plunger rod, such that the clock spring is tensioned upon rotation of the dose setting member;
   a hold and release member releasably connected to the drive member for holding the clock spring in a tensioned state and for releasing the clock spring from the tensioned state; and
   an activator having a distal end protruding through a distal passage of the dose setting member, and being interactively connected to the hold and release member such that when the activator is pushed in the proximal direction, the hold and release member is proximally moved, whereby the clock spring is released from its tensioned state, forcing the drive member to rotate; wherein the activator is connected through a center of the clock spring with the hold and release member on a proximal side of the clock spring; and the activator comprises an activation member having a distal end protruding through the distal passage of the dose setting member, and an activation sleeve coaxially arranged within the drive member, movable in relation to the drive member in a longitudinal direction through the center of the clock spring, and having a distal end co-acting with the activation member and a proximal end co-acting with the hold and release member.

2. The medicament delivery device of claim 1, wherein the second end of the clock spring is connected to the drive member through an intermediate member.

3. The medicament delivery device of claim 1, wherein the dose setting member has an opening through which a dose size indicium arranged on the drive member is visible.

4. The medicament delivery device of claim 1, wherein the tubular housing comprises a proximal housing part and a distal housing part interactively connected to each other, and the proximal housing part is configured for accommodating the medicament container.

5. The medicament delivery device of claim 4, wherein the driver comprises threads and longitudinal grooves arranged on an outer surface of the plunger rod, and radial outwardly directed protrusions on an inner surface of a central passage of the distal housing part are configured for co-acting with the grooves of the plunger rod, and threads on a central passage of the drive member are configured for co-operating with the threads of the plunger rod, such that the plunger rod is locked against rotation but is movable in the longitudinal direction.

6. The medicament delivery device of claim 5, wherein the inner surface of the distal housing part has a first holding device interactively co-acting with a corresponding first holding device of the dose setting member.

7. The medicament delivery device of claim 6, wherein the hold and release member comprises a second holding device releasably connected to a corresponding second holding device of the drive member, such that when the dose setting member is turned to set a dose, the clock spring is tensioned and held in a tensioned state by the first and the second holding devices.

8. The medicament delivery device of claim 7, wherein the first holding device on the inner surface of the distal housing part includes a circumferentially extending ratchet and the corresponding first holding device of the dose setting member includes a corresponding circumferentially extending ratchet, and the ratchets are configured such that the dose setting member is rotatable in only one direction and locked in a certain position when released.

9. The medicament delivery device of claim 8, wherein a distance between two consecutive teeth of the ratchets correspond to a dose increment.

10. The medicament delivery device of claim 9, wherein the dose setting member is resiliently movable in the longitudinal direction by a first resilient member configured between a circumferential ledge of the distal housing part and a proximal circumferential ledge of the dose setting member for forcing the ratchets in connection with each other, such that when the dose setting member is distally moved in relation to the distal housing part against the force of the second spring member, the ratchets move out of contact with each other and the dose setting member can be turned back to reset a dose.

11. The medicament delivery device of claim 6, wherein a second resilient member is configured between an annular ledge on the inner surface of the distal housing part and a proximal annular surface of the hold and release member, and the hold and release member includes longitudinally extending grooves and ledges interactively connected to corresponding longitudinally extending grooves and ledges on the inner surface of the distal housing part, such that when the activation member is pushed in the proximal direction, the hold and release member is proximally moved but rotationally locked, and when the activation member is released, the second resilient member forces the hold and release member, the activation sleeve and thereby the activation member to be distally moved.

12. The medicament delivery device of claim 4, wherein the second end of the clock spring is connected to the drive member through an intermediate member.

13. The medicament delivery device of claim 4, wherein the dose setting member has an opening through which a dose size indicium arranged on the drive member is visible.

14. A medicament delivery device, comprising:
a tubular housing configured for accommodating a medicament container, the tubular housing comprising a proximal housing part and a distal housing part interactively connected to each other; wherein the proximal housing part is configured for accommodating the medicament container;
a dose setting member rotatable in relation to the housing for setting a dose to be expelled;
a plunger rod configured for acting on a stopper inside the medicament container, such that a translational movement of the plunger rod in a proximal direction causes the dose to be expelled;
a driver that converts a rotational movement of the dose setting member into translational movement of the plunger rod, the driver comprising threads and longitudinal grooves arranged on an outer surface of the plunger rod;
a spiral-strip clock spring transverse to a longitudinal direction of the device having a first end connected to the dose setting member and a second end connected to a drive member interactively connected to the plunger rod, such that the clock spring is tensioned upon rotation of the dose setting member;
a hold and release member releasably connected to the drive member for holding the clock spring in a tensioned state and for releasing the clock spring from the tensioned state; and
an activator having a distal end protruding through a distal passage of the dose setting member, and being interactively connected to the hold and release member such that when the activator is pushed in the proximal direction, the hold and release member is proximally moved, whereby the clock spring is released from its tensioned state, forcing the drive member to rotate; wherein the activator is connected through a center of the clock spring with the hold and release member on a proximal side of the clock spring; and the activator comprises an activation member having a distal end protruding through the distal passage of the dose setting member, and an activation sleeve coaxially arranged within the drive member, having a distal end co-acting with the activation member and a proximal end co-acting with the hold and release member;
wherein radial outwardly directed protrusions on an inner surface of a central passage of the distal housing part are configured for co-acting with the grooves of the plunger rod, and threads on a central passage of the drive member are configured for co-operating with the threads of the plunger rod, such that the plunger rod is locked against rotation but is movable in the longitudinal direction.

15. The medicament delivery device of claim 14, wherein the inner surface of the distal housing part has a first holding device interactively co-acting with a corresponding first holding device of the dose setting member.

16. The medicament delivery device of claim 15, wherein the hold and release member comprises a second holding device releasably connected to a corresponding second holding device of the drive member, such that when the dose setting member is turned to set a dose, the clock spring is tensioned and held in a tensioned state by the first and the second holding devices.

17. The medicament delivery device of claim 16, wherein the first holding device on the inner surface of the distal housing part includes a circumferentially extending ratchet and the corresponding first holding device of the dose setting member includes a corresponding circumferentially extending ratchet, and the ratchets are configured such that the dose setting member is rotatable in only one direction and locked in a certain position when released.

18. The medicament delivery device of claim 17, wherein a distance between two consecutive teeth of the ratchets correspond to a dose increment.

19. The medicament delivery device of claim 18, wherein the dose setting member is resiliently movable in the longitudinal direction by a first resilient member configured between a circumferential ledge of the distal housing part and a proximal circumferential ledge of the dose setting member for forcing the ratchets in connection with each other, such that when the dose setting member is distally moved in relation to the distal housing part against the force of the second spring member, the ratchets move out of contact with each other and the dose setting member can be turned back to reset a dose.

20. The medicament delivery device of claim 15, wherein a second resilient member is configured between an annular ledge on the inner surface of the distal housing part and a proximal annular surface of the hold and release member, and the hold and release member includes longitudinally extending grooves and ledges interactively connected to corresponding longitudinally extending grooves and ledges on the inner surface of the distal housing part, such that when the activation member is pushed in the proximal direction, the hold and release member is proximally moved but rotationally locked, and when the activation member is released, the second resilient member forces the hold and release member, the activation sleeve and thereby the activation member to be distally moved.

* * * * *